United States Patent [19]

Huber et al.

[11] 4,322,215

[45] Mar. 30, 1982

[54] METHOD FOR DETERMINING PARTICULAR SPECIES OF CHLORINE IN A WATER SAMPLE

[75] Inventors: Calvin O. Huber, Mequon; Karl G. Schick, Whitefish Bay; Joel T. Coburn, Milwaukee, all of Wis.

[73] Assignee: Electric Power Research Institute, Inc., Palo Alto, Calif.

[21] Appl. No.: 200,046

[22] Filed: Oct. 23, 1980

[51] Int. Cl.³ ............................................... G01N 7/00
[52] U.S. Cl. ................................. 23/230 R; 204/1 T; 422/68
[58] Field of Search .......... 23/230 R; 204/1 T, 195 P; 422/68

[56] References Cited

U.S. PATENT DOCUMENTS 2,617,715 11/1952 Halle .................................. 23/230 R
3,413,199 11/1968 Morrow ............................ 23/230 R
4,049,382 9/1977 Ross et al. ......................... 23/230 R Primary Examiner—William F. Smith
Attorney, Agent, or Firm—Flehr, Hohbach, Test

[57] ABSTRACT

A technique for determining and distinguishing between specific species of chlorine in a supply of water is disclosed herein along with certain applicable apparatus. In carrying out this technique, one or more water samples are obtained from a larger supply and made to display a pH within a specific range. In a preferred embodiment, a sample is provided for each of the different species of chlorine to be determined. A predetermined amount of hydrogen peroxide is added to each of these samples. If hypochlorous acid and/or hypochlorite (one of the species to be determined) is present in any of the samples, the hydrogen peroxide by itself will react therewith for producing oxygen. If however either monochloramine or dichloramine (other chlorine species) is present, it is necessary to combine the hydrogen peroxide with a certain minimum amount of iodine, preferably in the form of potassium iodide, to produce an oxygen evolving reaction. Dichloramine requires a greater concentration of iodine than monochloramine and, hence, the two can be distinguished from one another. In each case, the produced oxygen is detected for determining whether any or all of these chlorine species are present in the water supply and the amounts thereof.

18 Claims, 5 Drawing Figures

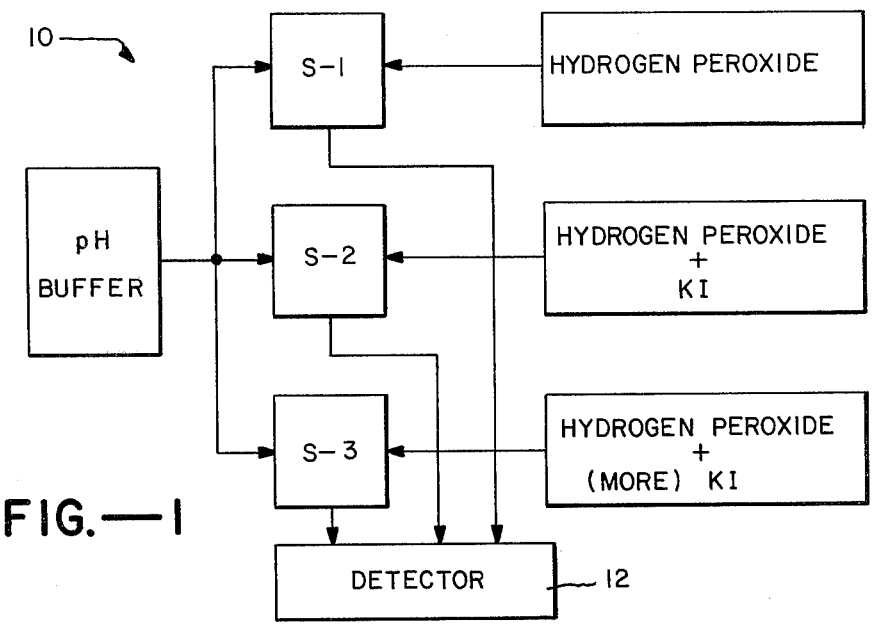
FIG.—1
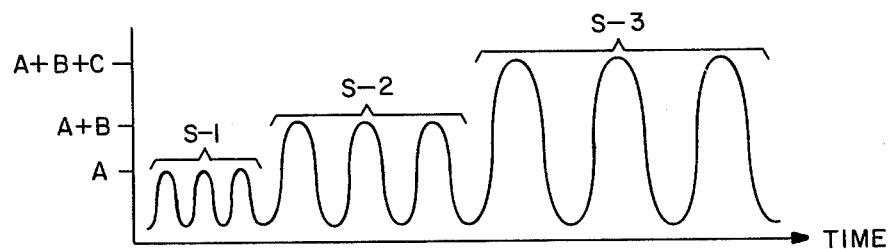
FIG.—2
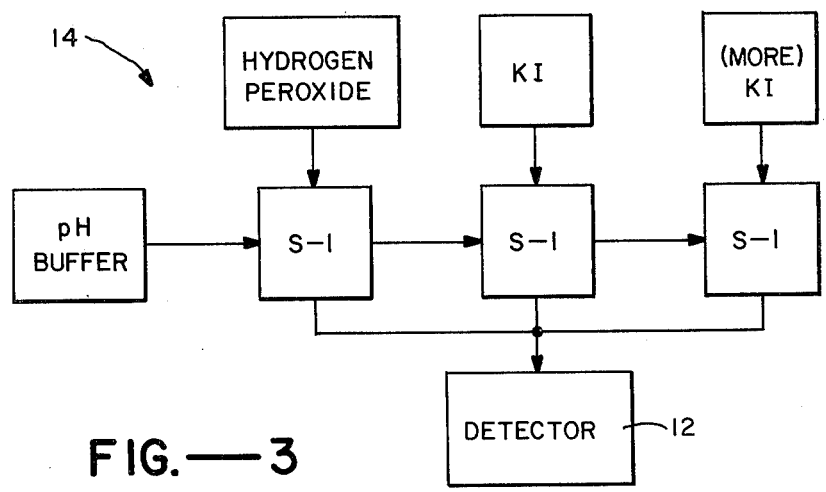
FIG.—3

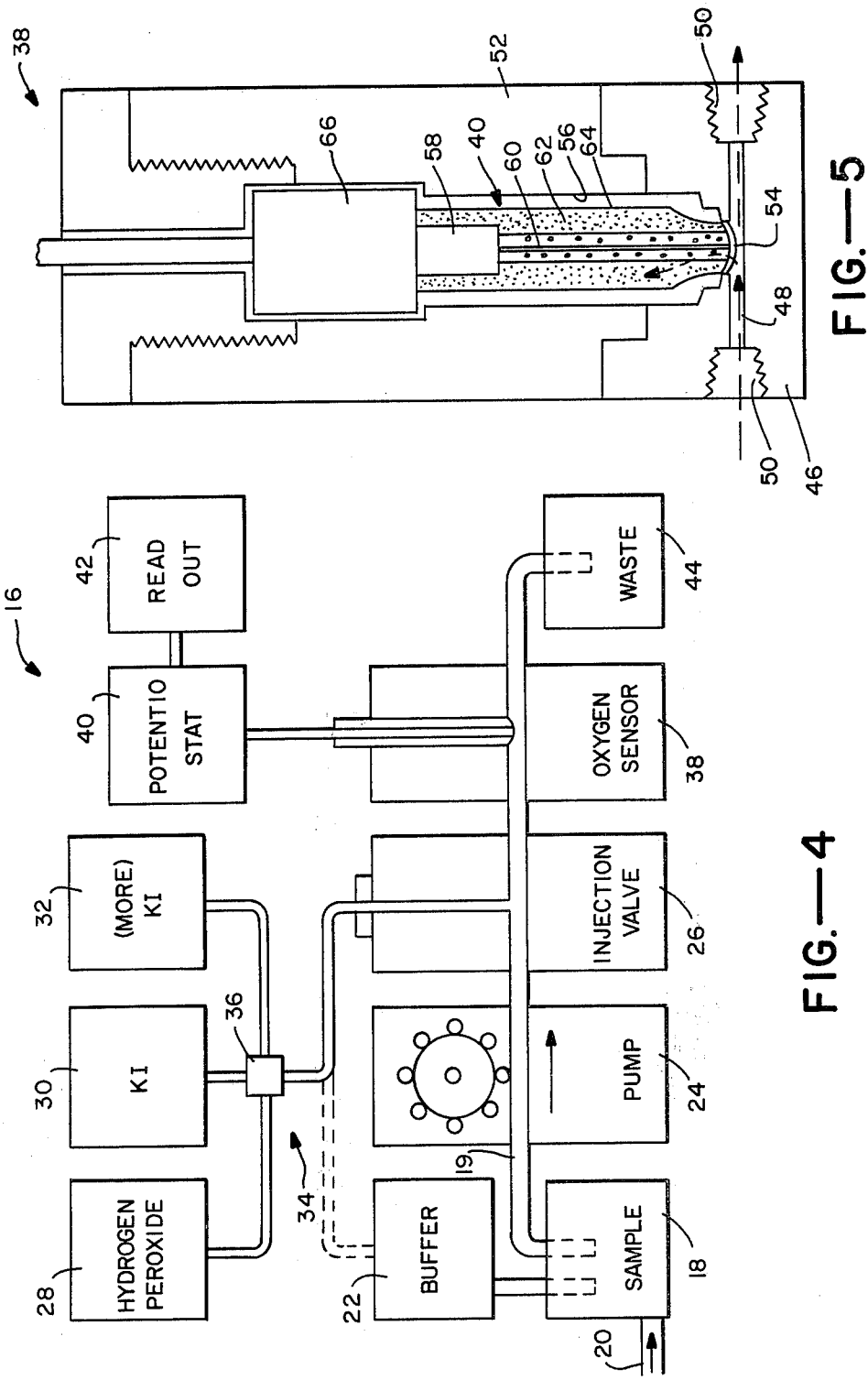

METHOD FOR DETERMINING PARTICULAR SPECIES OF CHLORINE IN A WATER SAMPLE

The present invention relates generally to techniques for analyzing given water supplies for chlorine and more particularly to a technique for determining and distinguishing between different specific species of chlorine in the water supplies.

From a water conservation standpoint and particularly for the purpose of protecting fresh water fish it has been found desirable to monitor for specific species of chlorine. Of particular interest are hypochlorous acid and/or hypochlorite (depending upon the pH of the water), monochloramine and dichloramine. It is therefore a specific object of the present invention to provide an uncomplicated, reliable and yet economical technique for determining and distinguishing between these three species of chlorine in a water supply.

Another specific object of the present invention is to provide a technique for determining and distinguishing between the particular chlorine species mentioned on a large scale so as to be practical for use by industries producing chlorine containing wastewater.

A more general object of the present invention is to provide a technique for determining a single specie of chlorine in a water sample, specifically a chlorine specie which reacts with hydrogen peroxide to produce oxygen, with or without the need for certain other additives.

As will be described in more detail hereinafter, the technique disclosed herein is one which requires providing one and preferably more than one water sample from the larger water supply being analyzed and maintaining these samples at a pH within a specific range, preferably between five and eight. A predetermined amount of hydrogen peroxide is added to the sample for causing the latter to react with the particular chlorine specie being sought, if the latter is present, to produce oxygen in the water sample or samples, preferably only dissolved oxygen. If hypochlorous acid and/or hypochlorite, its equivalent (depending upon the pH of the sample or samples), is present, the hydrogen peroxide will react therewith to produce the resultant oxygen without the need for other additives. On the other hand, if either monochloramine or dichloramine is present, for the latter to react with hydrogen peroxide to produce oxygen, it has been found necessary to add certain minimum amounts of iodine, preferably in the form of potassium iodide. In the case of dichloramine, a greater amount of iodine is necessary to produce the desired reaction than for monochloramine, depending upon the specific pH of the water sample. In any event, a suitable device is provided for detecting the oxygen if produced. In a preferred, practical embodiment a separate water sample is provided for each of the species being analyzed.

The present technique for determining and distinguishing between different species of chlorine in one or more water samples will be described in more detail hereinafter in conjunction with the drawings wherein:

FIG. 1 is a block diagram illustrating one technique for determining and distinguishing between particular species of chlorine in individual water samples;

FIG. 2 is a graphic display illustrating the detection of the specific chlorine species sought in the technique shown in FIG. 1;

FIG. 3 is a block diagram illustrating a second technique for determining said distinguishing between the same chlorine species associated with the FIG. 1 technique but using a single water sample;

FIG. 4 is a diagrammatic illustration of a preferred system for determining and distinguishing between particular species of chlorine in an overall water supply and specifically a system which is especially suitable for use on a large scale; and FIG. 5 is a view in vertical section of an oxygen sensing device comprising one component of the overall system shown in FIG. 4.

As stated briefly above and as will be described in more detail hereinafter, the present invention utilizes hydrogen peroxide ($H_2O_2$) as a primary component in determining and distinguishing between certain species of chlorine in a water supply. These chlorine species consist of hypochlorous acid and/or hypochlorite, monochloramine and dichloramine. In the case of hypochlorous acid and/or hypochlorite, the chlorine/hydrogen peroxide reaction is believed to involve the following steps:

In reaction step (1) above, whether hypochlorous acid and/or hypochlorite is present in the water sample depends upon the pH of the latter. If the pH is about eight or greater, hypochlorite will be present for the most part with little if any hypochlorous acid. At lower pH values, greater amounts of hypochlorous acid is present as opposed to hypochlorite. In this regard, since hypochlorite and hypochlorous acid are actually one in the same specie depending upon the pH of the water sample, for purposes of simplicity both will be referred to merely as hypochlorite with the understanding that the two may be present, either alone or together, depending upon the pH of the particular water sample in question. In any event, this specific chlorine specie is reduced by hydrogen peroxide to ultimately produce oxygen, without the need for any other additives, as seen in reaction step (2). As a result of this reaction, a suitable device can be provided for detecting the oxygen and thereby monitoring the presence or absence of hypochlorous acid and/or hypochlorite, as will be discussed in more detail hereinafter. In a preferred embodiment of the present invention, the amount of hydrogen peroxide initially provided is selected so that all of the oxygen produced is dissolved in the water sample so that an appropriate device, specifically a commercially available amperometric oxygen probe can be used to detect the dissolved oxygen (referred to as $pO_2$) if present and the quantity present. In this latter regard, it is important to determine the quantity of oxygen produced since this value corresponds directly to the amount of hypochlorite in the sample. More specifically, as will be discussed in more detail below, it has been found that the steady state production of oxygen ($\Delta pO_2$) and the initial rate response ($\Delta pO_2/sec$) are directly related to chlorine concentration. Because of this, it should be apparent that the measurements must be carried out under anaerobic reaction conditions.

In performing various analytical tests relating to the reaction of hydrogen peroxide and hypochlorite, it was not only determined that there is a quantitative relationship between the hypochlorite present and the dissolved oxygen produced but that both the steady state and initial rate measurements are strongly pH dependent, so long as the pH of the water sample is at approximately eight or below. Within this pH range the greatest increase occurs between a pH of five and eight. Beyond a pH of eight, the $O_2$ formation reaction is pH independent and hence is preferred. In any event, it has been found desirable to control the pH of the sample, preferably at a fixed value between a pH of five and eight and most preferably at a pH of about eight. This may be accomplished by providing a standard buffer solution at the desired pH and combining this solution in sufficient quantity with the sample in question so that the latter (e.g. the combination) displays the same pH.

In further evaluating the reaction between hydrogen peroxide and water samples containing hypochlorite, it was found that at a fixed hydrogen peroxide concentration (1.0 mM), the increase in steady state $pO_2$ changes linearly with hypochlorite solution. Initial rate experiments carried out at a constant hydrogen peroxide concentration and variable hypochlorite concentration were used to generate log (initial rate) versus log (HOCl) plots. These plots exhibited a slope of 1.0 for samples at both a pH of eight and at a pH of five, indicating that the reaction is indeed first order with respect to hypochlorite species. A similar experiment was carried out for a constant HOCl concentration and a variable hydrogen peroxide concentration. The results of the latter experiment indicated a first order reaction with respect to the hydrogen peroxide.

With further reference to the reaction between hydrogen peroxide and hypochlorite, it has been found that a preferred technique for determining whether or not hypochlorite is present in a water sample (and the amount if present) utilizes a sufficient amount of hydrogen peroxide to provide a concentration level of $10^{-3}$ M. In this preferred technique, the sample itself is maintained at a pH of eight in a phosphate buffer. Responses to hypochlorite using this technique were observed down to 0.03 ppm Cl in the sample tested. An upper detection limit of approximately 75 ppm Cl has also been observed. This upper detection limit is due to oxygen solubility limitations, i.e., at $[OCl^-]$ greater than 75 ppm, the solution becomes oxygen saturated, resulting in additionally produced oxygen leaving the solution. If the overall detection scheme is capable of not only measuring the dissolved oxygen but also free oxygen gas in the case where the sample is saturated, the present technique would not necessarily be confined to an upper limit.

In contrast to the foregoing reaction between hydrogen peroxide and hypochlorite (or hypochlorous acid), no reaction occurs between hydrogen peroxide and either monochloramine or dichloramine in the absence of iodine, preferably in the form of potassium iodide (KI). More specifically, it has been found that in the presence of small amounts of potassium iodide ($10^{-3}$ M), monochloramine rapidly oxidizes hydrogen peroxide. In the presence of monochloramine and potassium iodide, the hydrogen peroxide oxidation reaction is believed to involve the following steps:

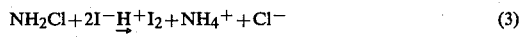

$$NH_2Cl + 2I^- \underset{}{\overset{H^+}{\rightarrow}} I_2 + NH_4^+ + Cl^- \quad (3)$$

$$I_2 + H_2O_2 \rightarrow O_2 + 2I^- + 2H^+ \quad (4)$$

From reaction step (4) above, it should be apparent that the reaction just described results in the production of oxygen gas. In initial work done in this area, it was found that at fixed hydrogen peroxide and potassium iodide concentrations, the initial rate response ($\Delta pO_2$/sec) as well as the steady state response ($\Delta pO_2$) were found to change linearly with monochloramine concentration. At fixed hydrogen peroxide and monochloramine concentrations, the initial rate of $\Delta pO_2$ was found to be linearly related to the potassium iodide concentration whereas the steady state response was found to be independent of potassium iodide concentration. In the absence of monochloramine, no $O_2$ was generated in a buffer solution (pH 8.0) containing both hydrogen peroxide and potassium iodide. Initial rate experiments carried out at constant $H_2O_2$ and KI concentrations with variable $NH_2Cl$ concentrations were used to generate log (initial rate) versus log ($NH_2Cl$) plot. The plot exhibited a slope of 1.0 at pH 8.0, indicating that the reaction is first order with respect to $NH_2Cl$. In addition, in this initial work, it was learned that monochloramine and dichloramine can be differentiated by the pH of the sample containing these chlorine species and the potassium iodide concentration provided.

In subsequent experiments it was observed that a linear signal (quantities of oxygen produced) is generated in accordance with the concentration level of the monochloramine for concentrations ranging from 0.08 to 5 ppm Cl. The signal measured for monochloramine has been found to have no contribution for dichloramine so long as the potassium iodide concentration level remains at or below a certain level, specifically about $10^{-3}$ M in the samples tested. On the other hand, by providing a greater concentration of potassium iodide, specifically a concentration level of about $5 \times 10^{-2}$ M, in a sample displaying a pH of about eight, the dichloramine, if present, reacts with the hydrogen peroxide to produce oxygen in the same manner as monochloramine and hypochlorite. In an actual example, a water sample having dichloramine therein was maintained at a pH of 8.0 using a phosphate buffer and sufficient hydrogen peroxide was provided to maintain a concentration level of $10^{-3}$ M. In addition, sufficient potassium iodide was provided for maintaining a concentration level of about $10^{-2}$ M. This resulted in the observation of a linearity of signal versus concentration of dichloramine from 0.2 to 0.7 ppm Cl.

With further reference to the reaction between hydrogen peroxide and the chloramine species, it should be apparent that both can be distinguished from hypochlorite (or hypochlorous acid) by adding a certain minimum amount of iodine to the sample. It should also be apparent that monochloramine and dichloramine can be distinguished from one another by the amount of iodine used. While an exact amount of iodine and hydrogen peroxide necessary to accomplish this along with a particular pH of the solution have been suggested, it should be apparent that variations of one or all of these parameters will cause the others to vary. For example, a lower pH than eight for the solution may cause a change in the concentration levels of potassium iodide necessary to make the appropriate distinctions. Nevertheless, one could readily determine these parameters based on the teachings herein.

Having described the foregoing ways of determining and distinguishing between the three specific chlorine species discussed above in a water sample, attention is now directed to various suggested systems for carrying out this technique. To this end, reference is first made to FIG. 1 which illustrates one such system generally designated by the reference numeral 10. As seen there, this system includes three distinct water samples S-1, S-2 and S-3 which may be taken from a single larger supply (not shown). Each of these samples is combined with a buffer solution to maintain its pH at a desired level, for example at eight, as indicated in FIG. 1. In the case of sample S-1, the prescribed amount of hydrogen peroxide alone is added thereto. This particular solution is free of any iodine. As a result, only the hypochlorite and/or hypochlorous acid, if present, and the hydrogen peroxide react to produce the previously described oxygen. In the case of sample S-2, both hydrogen peroxide and potassium iodide in the prescribed amounts are introduced therein for causing the hypochlorite and/or monochloramine, if present, to react with the hydrogen peroxide to produce its own resultant oxygen. Finally, in the case of the sample S-3, the prescribed amounts of hydrogen peroxide and potassium iodide are provided therein for causing the hypochlorite, monochloramine and dichloramine to react with the hydrogen peroxide for producing its own oxygen.

System 10 also includes an oxygen detector 12 which will be discussed in more detail hereinafter with respect to FIGS. 4 and 5. For the moment, it should suffice to say that this detector serves to detect oxygen produced as a result of the previously described reactions in samples S-1, S-2 and S-3. In this regard, in order to not only determine which if any of the three previously described chlorine species is present in the water supply used to provide the samples but also the quantities thereof, it is necessary to evaluate each of the samples separately. This is because the oxygen generated as a result of the presence of the species are additive. More specifically, when hydrogen peroxide alone is added to the sample S-1, a specific amount of oxygen is generated, depending upon the amount of hypochlorite and/or hypochlorous acid present. In the graphic illustration of FIG. 2 which shows time versus the peak oxygen level detected by detector 12, the first three peaks correspond to the amount of oxygen detected as a result of the reaction in sample S-1. Note that this peak value is indicated at A. Thereafter, when the prescribed amounts of hydrogen peroxide and potassium iodide are added to sample S-2, the amount of oxygen detected is shown in FIG. 2 to be equal to the level A+B, that is, an amount A contributed by the hypochlorite present and an amount B contributed by the monochloramine. In sample S-3, when the prescribed amounts of hydrogen peroxide and potassium iodide are added, the total amount of oxygen detected is A+B+C, that is, an amount A corresponding to the hypochlorite in the sample, an amount B corresponding to the monochloramine in the sample and an amount C corresponding to the amount of dichloramine.

From the foregoing, it should be apparent that if the graphic illustration of FIG. 2 represents oxygen generating reactions sufficient to depleat reproducible amounts of the reacting chlorine species in the various samples S-1, S-2 and S-3, a quantitative analysis of these species can be made. More specifically, from the analysis of sample S-1, the exact amount of hypochlorite and/or hypochlorous acid can be determined. From sample S-2, the amount of this latter specie and monochloramine together can be determined and therefore, based on the results of sample S-1, the amount of monochloramine alone can be determined. In the same manner, from sample S-3, the amount of dichloramine alone can be determined. As stated above, each sample must be maintained at a specific pH, preferably at about eight, a sufficient amount of hydrogen peroxide must be provided and the proper amount of potassium iodide must also be used, depending upon whether monochloramine or dichloramine is being sought.

Referring to FIG. 3, attention is directed to a second system 14 for accomplishing the same end result as system 10, that is, for determining and distinguishing between the three previously described chlorine species in a water supply. In system 14, a single sample S-1 is initially provided at a precontrolled pH level, as indicated diagrammatically by the pH buffer added thereto. Like system 10, the sample S-1 in system 14 is combined with only hydrogen peroxide (in the absence of potassium iodide) so to cause an oxygen producing reaction between the hydrogen peroxide and hypochlorite, if the latter is present. The oxygen produced is detected by the same type of detector 12 used in system 10 and the results may be graphically illustrated in the same manner shown in FIG. 2, e.g. as the level A shown there. However, instead of providing second and third distinct samples as in system 10, system 14 uses the same sample S-1 to detect for monochloramine and dichloramine. In the case of monochloramine, after the hypochlorite has been detected for, hydrogen peroxide in the prescribed amount is again provided in the sample (assuming an excess amount was not initially added) in combination with the prescribed amount of potassium iodide for causing all of the monochloramine to react therewith for producing oxygen. This oxygen is also detected but unlike system 10, the amount detected in system 14 corresponds only to the monochloramine (amount B in FIG. 2) since the hypochlorite has already been exhausted. In order to test for dichloramine, the same sample is thereafter provided with still another prescribed amount of hydrogen peroxide (again assuming an excess is not present) in combination with the prescribed amount of potassium iodide for causing all of the dichloramine in the sample to react for producing oxygen. This oxygen is detected and corresponds only to the amount of dichloramine present in the sample (e.g., the amount C).

Referring now to FIG. 4, attention is directed to still another system for determining and distinguishing between the previously described chlorine species and specifically a system which is especially suitable for use in large scale. This system which is generally indicated by the reference numeral 16 includes a reservoir 18 for containing a water sample to be analyzed therein. This container may be designed to house a discrete sample or, as indicated diagrammatically at 20, it may be designed for housing a continuously periodically replenished sample from a larger water supply not shown. A separate reservoir 22 containing a buffer solution at a predetermined pH is placed in fluid communication with container 18 for combining the buffer solution with the sample for maintaining the pH level of the combination at a predetermined level, for example at a pH of eight.

A subsample of the combination sample just described is pumped or otherwise conveyed through tube means 19 by suitable means 24 into an injection valve 26. As shown in FIG. 4, the means 24 is a peristaltic pump. The injection valve may be constructed of any suitable means capable of injecting hydrogen peroxide and/or potassium iodide into the subsample as the latter passes therein. In a preferred embodiment, system 16 includes three separate and distinct reservoirs 28, 30 and 32 for respectively containing hydrogen peroxide alone, hydrogen peroxide in combination with potassium iodide (at a prescribed concentration level) and hydrogen peroxide in combination with potassium iodide (at a different prescribed concentration level). Suitable means generally indicated at 34 including an appropriate metering valve generally indicated at 36 and control components (not shown) are provided for alternatively placing the three reservoirs 28, 30 and 32 in fluid communication with the injection valve 26 for selectively metering predetermined amounts of the additives contained in these reservoirs into the subsample passing into the injection valve. For example, in the case of a first subsample, the valve 36 can be controlled to cause the prescribed amount of hydrogen peroxide from reservoir 28 to be injected into the subsample as the latter passes into the injection valve. At the same time, the buffer could and preferably would be combined with the subsamples at valve 26 rather than at reservoir 18, as indicated by dotted lines in FIG. 4. The means 24 thereafter causes the subsample to pass into oxygen sensor 38 which will be described in more detail with respect to FIG. 5. This oxygen sensor serves to detect the amount of oxygen produced as a result of the reaction between the hydrogen peroxide and any hypochlorite in the subsample. A conventional potentiostat 40 is coupled to the sensor and serves as a transducer for converting the detected oxygen to an electrical current which, in turn, is used to drive a readout 42 for providing a visual and/or permanent display corresponding to the amount of oxygen detected. The first subsample is thereafter pumped or otherwise delivered into a waste container 44.

Having quantitatively analyzed the first subsample of water for hypochlorite, as described above, pump 24 serves to direct a second subsample through to injection valve 26. At the same time, means 34 controls metering valve 36 so as to cause the prescribed amount of hydrogen peroxide and potassium iodide to be injected from the reservoir 30 into the injection valve so as to mix with the second subsample. This second subsample then passes into the oxygen sensor 38 where the oxygen generated thereby is detected and readout. The second subsample is then pumped into waste container 44. This procedure is again repeated for a third subsample. However, in this latter case, means 34 causes the injection valve 36 to inject the prescribed amount of hydrogen peroxide/potassium iodide from container 32 into the injection valve while the third sample is therein. This mixture is immediately thereafter pumped into the oxygen sensor where the generated oxygen is detected and readout. Finally, the third sample is pumped into waste container 44.

From the foregoing, it should be apparent that overall system 16 functions in the same way as previously described system 10 to provide corresponding levels of detected oxygen A, A+B and A+B+C so that hypochlorite, monochloramine and dichloramine can be quantitatively determined.

Referring now to FIG. 5, attention is directed to a specific oxygen sensor which, as stated previously, is preferably a commercially available amperometric oxygen probe. This probe is shown including a stainless steel base 46 defining an inner chamber 48 in the form of a through channel for receiving and passing therethrough the previously described subsamples of water from container 18. In this regard, opposite ends of the chamber 48 are placed in fluid communication with enlarged, internally threaded bores 50 adapted to receive cooperating ends of tube means 19 serving to carry the flow of sample water as described above.

Probe 38 includes a main body 52 fixedly connected with base 46 for containing an oxygen permeable membrane 54 and the previously described potentiostat 40. The membrane itself is constructed of a suitable material, for example Teflon (a trademark of DuPont) and extends entirely across the bottom opening of an overall chamber 56 defined by space 46 in combination with main body 52. The membrane cooperates with the subsample located within chamber 48 to cause the oxygen produced therein to pass into chamber 56.

Potentiostat 40 is located within chamber 56 and is comprised of an anode 58, a cathode 60 and an aqueous solution of potassium chloride 62 within its own container 64. These components in conjunction with suitable electronic components (not shown) contained within housing 66 convert the oxygen entering chamber 56 into a corresponding parent signal for driving previously recited readout 42.

At stated previously, the entire probe and potentiostat belong with the readout device and previously described pump 24 and injection valve 26 may be conventional components. This is equally true of means 34 including its metering valve 36 and the control means associated therewith. Moreover, while not shown, a suitable means for detecting $O_2$ gas (out of solution) could be readily provided if the samples are analyzed in excess of their $O_2$ saturation levels.

What is claimed is:

1. A method for determining a particular specie of chlorine in a water sample, said method comprising the steps of: providing said sample at a pH within a specific range; adding a predetermined amount of hydrogen peroxide to said sample for causing the latter to react with said chlorine specie if present to produce oxygen; and detecting said oxygen if produced for indicating the presence of said specie.

2. A method according to claim 1 wherein the chlorine specie to be determined is hypochlorous acid and/or hypochlorite depending upon the pH of said water sample and wherein said water sample is provided without and is free of potassium iodide whereby to distinguish said hypochlorous acid and/or hypochlorite if present from monochloramine and dichloramine if the latter two chlorine species also happen to be present in said sample.

3. A method according to claim 2 wherein said sample is provided at a pH of between five and eight.

4. A method according to claim 3 wherein said hydrogen peroxide is provided in said water sample at a concentration of about $10^{-3}$ M.

5. A method according to claim 1 wherein the chlorine specie to be determined is one of monochloramine or dichloramine and wherein a predetermined amount of potassium iodide is added to said water sample whereby to detect said monochloramine or dichloramine species if present from hypochlorous acid and/or hypochlorite if the latter chlorine specie also happens to be present in said sample.

6. A method according to claim 5 wherein said sample is provided at a pH of between about five and eight.

7. A method according to claim 6 wherein said potassium iodide is provided in said water sample at one of two different specific concentration levels whereby to detect for a specific one of said monochloramine and dichloramine species.

8. A method according to claim 7 wherein the chlorine specie to be determined is monochloramine and wherein the concentration level of potassium iodide provided in said water sample is about $10^{-3}$ M.

9. A method according to claim 7 wherein the chlorine specie to be determined is dichloramine and wherein the concentration level of potassium iodide provided in said water sample is about $10^{-2}$ M.

10. A method according to claim 1 wherein all of said oxygen produced includes oxygen which is dissolved in said sample and wherein said detecting means includes for detecting said dissolved oxygen.

11. A method according to claim 10 wherein said oxygen produced consists of said dissolved oxygen.

12. A method for determining chlorine species from a group consisting of hypochlorous acid and/or hypochlorite, monochloramine and dichloramine in respective first, second and third samples of a larger supply of water, said method comprising the steps of: providing each of said samples at a pH within a specific range; placing a predetermined amount of hydrogen peroxide in each of said samples; providing said first sample free of potassium iodide whereby said hypochlorous acid and/or hypochlorite if present will react with said hydrogen peroxide to produce oxygen but said monochloramine and dichloramine if also present will not react with said hydrogen peroxide to produce oxygen; placing a first predetermined amount of potassium iodide in said second water sample for causing said monochloramine and not said dichloramine to react with said hydrogen peroxide and potassium iodide for producing additional oxygen; placing a second predetermined amount of potassium iodide in said third water sample for causing said dichloramine to react with said hydrogen peroxide and said potassium iodide for producing still further oxygen; and detecting from each of said sample oxygen for indicating whether or not any of said chlorine species are present in said water supply.

13. A method according to claim 12 wherein said each of said samples is provided at a pH of between about five and eight and wherein said hydrogen peroxide is provided in each of said samples at a concentration level of about $10^{-3}$ M.

14. A method according to claim 13 wherein said potassium iodide is provided in said second sample at a concentration level of about $10^{-3}$ M and in said third sample at a concentration level of about $5 \times 10^{-2}$ M.

15. A method according to claim 12 wherein all of said oxygen produced is dissolved in said samples and wherein said detecting means includes means for detecting said dissolved oxygen.

16. A method according to claim 12 wherein said samples are maintained at a particular pH by the step of adding buffer solutions of said particular pH thereto in sufficient quantities to cause the overall samples to display said pH.

17. A method according to claim 16 wherein said particular pH is about eight.

18. A method for determining chlorine species from a group consisting of hypochlorous acid and/or hypochlorite, monochloramine and dichloramine in a single sample of water, said method comprising the steps of: providing said sample at a pH within a specific range; placing a predetermined amount of hydrogen peroxide in said sample; thereafter, initially maintaining said sample free of potassium iodide whereby said hypochlorous acid and/or hypochlorite if present will react with hydrogen peroxide to produce an initial amount of oxygen but said monochloramine and dichloramine if also present will not react with said hydrogen peroxide to produce an initial amount of oxygen; detecting for said initial amount of oxygen to indicate the presence or absence of said hypochlorous acid and/or hypochlorite; thereafter placing a first predetermined amount of potassium iodide in said water sample for causing said monochloramine and not said dichloramine to react with said hydrogen peroxide and potassium iodide for producing a second, additional amount of oxygen; detecting for said additional amount of said oxygen if present to indicate the presence or absence of monochloramine; thereafter placing a second predetermined amount of potassium iodide in said water sample for causing said dichloramine to react with said hydrogen peroxide and said potassium iodide for producing a third amount of oxygen; and detecting for said third amount of oxygen if present to indicate the presence or absence of said dichloramine.

* * * * *

UNITED STATES PATENT AND TRADEMARK OFFICE
CERTIFICATE OF CORRECTION

PATENT NO. : 4,322,215
DATED : March 30, 1982
INVENTOR(S) : Calvin O. Huber, et al.

It is certified that error appears in the above-identified patent and that said Letters Patent are hereby corrected as shown below:

On The Title Page item (73) should read

--[73] Assignees: Wisconsin Alumni Research Foundation, Madison, Wisconsin and Electric Power Research Institute, Inc., Palo Alto, California--

Signed and Sealed this

Twenty-sixth Day of October 1982

[SEAL]

Attest:

GERALD J. MOSSINGHOFF

Attesting Officer   Commissioner of Patents and Trademarks